US008220082B2

(12) United States Patent
Chen

(10) Patent No.: US 8,220,082 B2
(45) Date of Patent: Jul. 17, 2012

(54) FAR-INFRARED HYDROTHERAPY DEVICE

(75) Inventor: Kuo-Kang Chen, Taipei (TW)

(73) Assignee: Rosace International Co., Ltd., Taipei (TW)

( * ) Notice: Subject to any disclaimer, the term of this patent is extended or adjusted under 35 U.S.C. 154(b) by 541 days.

(21) Appl. No.: 12/554,960

(22) Filed: Sep. 7, 2009

(65) Prior Publication Data

US 2011/0056012 A1 Mar. 10, 2011

(51) Int. Cl.
*A47K 3/00* (2006.01)
*A61H 33/02* (2006.01)

(52) U.S. Cl. .......................................... 4/541.4; 4/541.1

(58) Field of Classification Search ......... 4/541.1–541.6
See application file for complete search history.

(56) References Cited

U.S. PATENT DOCUMENTS

| | | | | |
|---|---|---|---|---|
| 6,317,903 | B1 * | 11/2001 | Brunelle et al. | 4/541.4 |
| 6,523,192 | B1 * | 2/2003 | Gloodt | 4/541.1 |
| 7,060,180 | B1 * | 6/2006 | Barnes | 4/541.1 |
| 2009/0089924 | A1 * | 4/2009 | Jan | 4/541.5 |

* cited by examiner

*Primary Examiner* — Tuan N Nguyen
(74) *Attorney, Agent, or Firm* — patenttm.us

(57) ABSTRACT

A far-infrared hydrotherapy device has a bath unit, an oxygen supplier, a booster pump, a pressure modulator and an acupressure jet. The bath unit has a tub, an outlet pipe and a heat pump. The tub is for accommodating a liquid. The outlet pipe is connected to the tub to allow the liquid to flowing through. The heat pump is connected to the tub and has a temperature controller. The oxygen supplier is connected to the outlet pipe and provides oxygen to the liquid. The booster pump is connected to the outlet pipe to elevate pressure of the liquid. The pressure modulator is connected to an outlet of the booster pump and has a pressure-equalizing device, a water pressure modulating valve, a pressure-stabilizer and a hose sequentially connected. The acupressure jet is connected to the hose and has an outlet. The far-infrared hydrotherapy device is useful for hydrotherapy.

16 Claims, 3 Drawing Sheets

40
411
421
30
41
42
50
40
43
10
44
20
30
50
11
12
511
51
55
53
52
512
54
60
d

FAR-INFRARED HYDROTHERAPY DEVICE

BACKGROUND OF THE INVENTION

1. Field of the Invention

The present invention relates to a hydrotherapy device, particularly a hydrotherapy device for massaging meridians and acupuncture points.

2. Description of the Prior Arts

Hydrotherapy is a physical therapy for treating diseases associated with muscles, skeleton or the like by using various physical properties of water to treat diseases, stimulate blood circulation and expel wastes or toxins from human body. Hippocrates, the Farther of Western Medicine, treated disease by using hot springs. Till 18th to 19th century, Sebastian Kneipp, Father of Hydrotherapy in Germany, employed hydrotherapy as formal medical tool.

In the East, hydrotherapy is usually employed in combination with Chinese medicine. The human body is an organism consisting of an exterior part, an interior part having organs and tissues within the interior part intimately connecting with each other. Meridians are mechanisms to maintain viability of the human body. Meridians go along Organs (Zang Fu) and extend to the exterior part of the human body. In Chinese medicine, it is believed that meridians can provide energy and maintain homeostasis of the body.

Chinese medicine is based upon the theory of five Zangs and six Fus. The five Zangs are name Heart, Liver, Spleen, Lungs and Kidneys. The six Fus are named Small Intestines, Gall Bladder, Stomach, Large Intestine, Urinary Bladder and Triple Heater. Each Zang or Fu corresponds to one related meridian. There are 14 main meridians in human body including meridians corresponding to five Zangs and six Fus and remaining three meridians, Pericardium Meridian, Ren Meridian and Du Meridian. Each meridian has several acupuncture points. Acupuncture is to stimulate acupuncture point on meridian to transfer energy to the corresponding Zang or Fu for treating diseases.

Current hydro-acupuncture devices are incapable of increasing dissolution of oxygen in water and generating far-infrared rays.

To satisfy the requirement, the present invention provides a hydrotherapy device to mitigate or obviate the aforementioned problems.

SUMMARY OF THE INVENTION

The main objective of the present invention is to provide a hydrotherapy device capable of modulating pressure of water for massaging acupuncture points and meridians, increasing dissolution of oxygen in water and generating far-infrared rays.

The present invention provides a far-infrared hydrotherapy device comprising a bath, an oxygen supplier, a booster pump, a pressure modulator and an acupressure jet.

The bath unit has a tub, an outlet and a heat pump. The tub has a container for accommodating a liquid. The outlet pipe is connected to the tub and communicates with the container to allow the liquid to flow. The heat pump is connected to the tub and has a temperature controller for controlling heat exchange between the heat pump and the liquid within the tub.

The oxygen supplier is connected to the outlet pipe and provides oxygen to the liquid.

The booster pump is connected to the outlet pipe to elevate pressure of the liquid and has an outlet.

The pressure modulator is connected to the outlet of the booster pump and has a pressure-equalizing device, a pressure modulating valve, a pressure-stabilizer and a hose. The pressure-equalizing device, the water pressure modulating valve, the pressure-stabilizer and the hose are sequentially connected.

The acupressure jet is connected to the hose and has an inlet. The inlet is connected to a tip of the hose and an outlet for the liquid flowing out.

Other objectives, advantages and novel features of the invention will become more apparent from the following detailed description when taken in conjunction with the accompanying drawings.

DETAILED DESCRIPTION OF THE PREFERRED EMBODIMENTS

Figure 1:
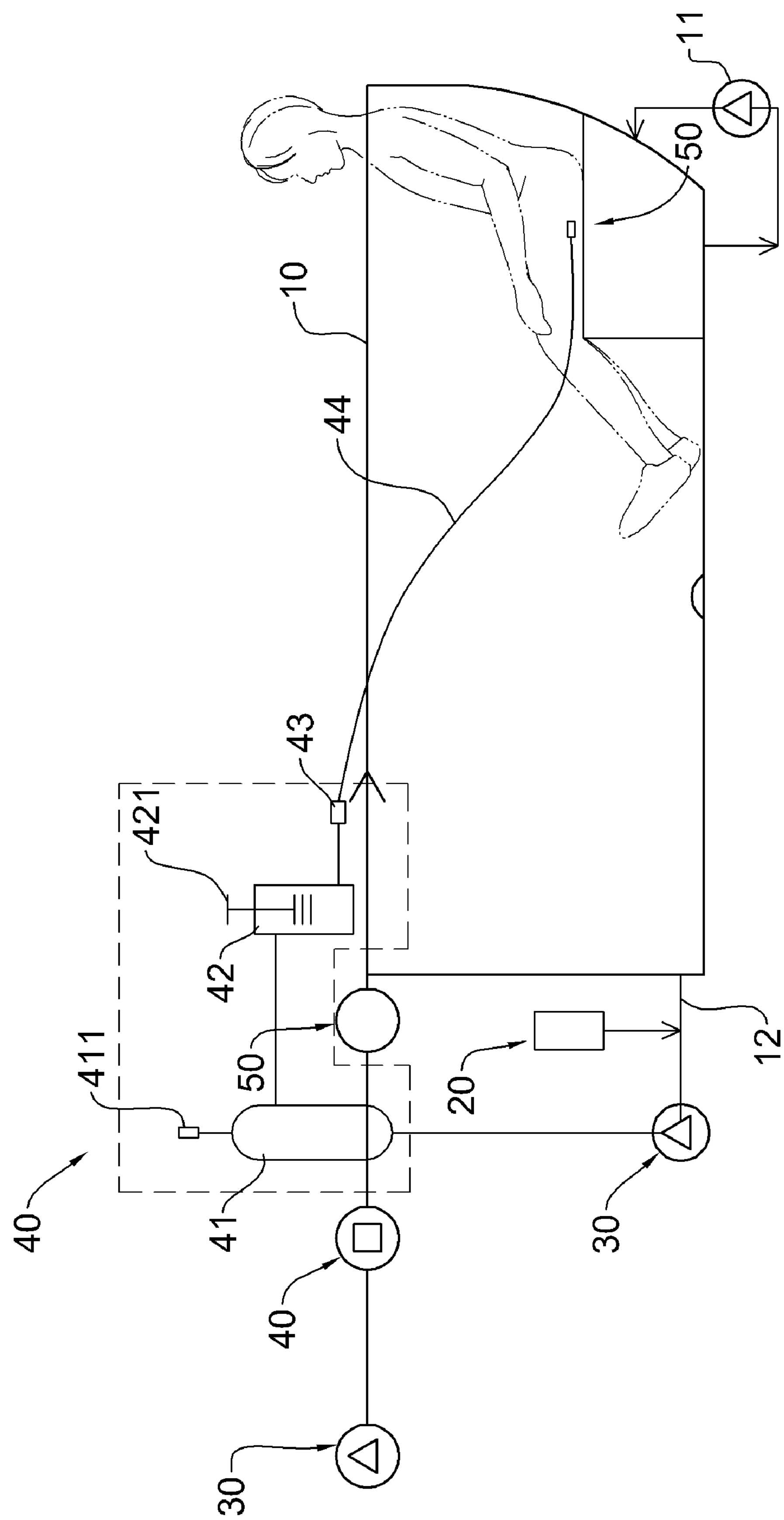
FIG. 1 is a scheme of the far-infrared hydrotherapy device in accordance with the present invention.
Figure 2:
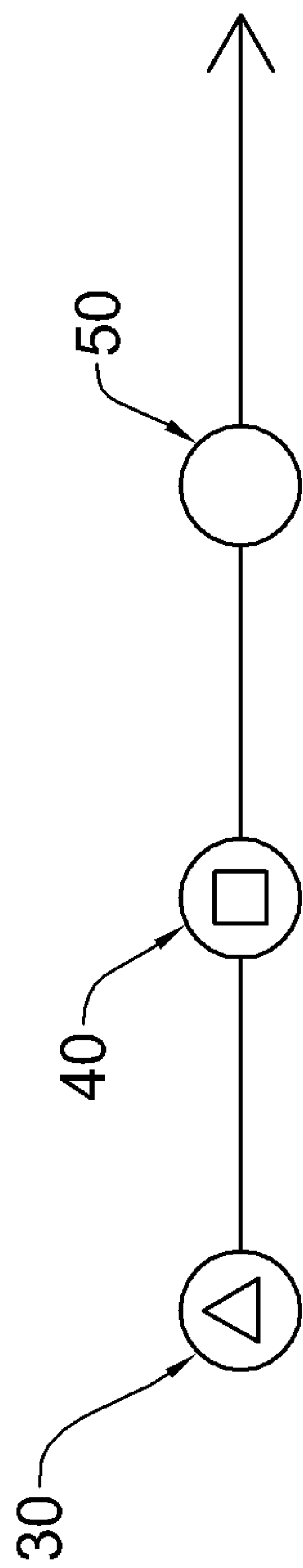
FIG. 2 is a scheme of combination of a booster pump, a pressure modulator and an acupressure jet of the far-infrared hydrotherapy device in FIG. 1.

With reference to FIGS. 1 and 2, a far-infrared hydrotherapy device in accordance with the present invention comprises a bath unit, an oxygen supplier (20), a booster pump (30), a pressure modulator (40) and an acupressure jet (50).

The bath unit has a tub (10), a heat pump (11) and an outlet pipe (12). The tub (10) has a container for accommodating a liquid and allow a subject to sit or lie therein. The heat pump (11) has an input end, an output end and a temperature controller. The input end and output end of the heat pump (11) are connected to the tub (10). The temperature controller determines heat exchange between heat pump (11) and the liquid in the tub (10) to adjust liquid in the tub (10) to a temperature range from 10~20° C., 20~30° C. or 30~40° C. The outlet pipe (12) has a first end and a second end. The first end of the outlet pipe (12) communicates with the container within the tub (10).

The oxygen supplier (20) is connected to the outlet pipe (12) and provides oxygen to the outlet pipe (12) to mix with liquid in the outlet pipe (12).

The booster pump (30) has an inlet and an outlet. The inlet of the booster pump (30) is connected to the second end of the outlet pipe (12). The liquid flows in the booster pump (30) and to elevate the pressure of the liquid to pressure P1 and flows out through the outlet of the booster pump (30).

The pressure modulator (40) is connected to the outlet of the booster pump (30) and has a pressure-equalizing device (41), a water pressure modulating valve (42), a pressure-stabilizer (43) and a hose (44). The pressure-equalizing device (41), the water pressure modulating valve (42), the pressure-stabilizer (43) and the hose (44) are sequentially connected. The pressure-equalizing device (41) has an air valve (411) for releasing extra oxygen. The water pressure modulating valve (42) has an adjusting bolt (421) for forming a water with dispersed oxygen. The hose (44) has a connecting end and a tip. The connecting end is connected to the water pressure modulating valve (42). The water-oxygen solution formed by the water pressure modulating valve (42)

finally flows into the pressure-stabilizer (43) and hose (44), resulting in a flow with an appropriate pressure P2.

Figure 3:
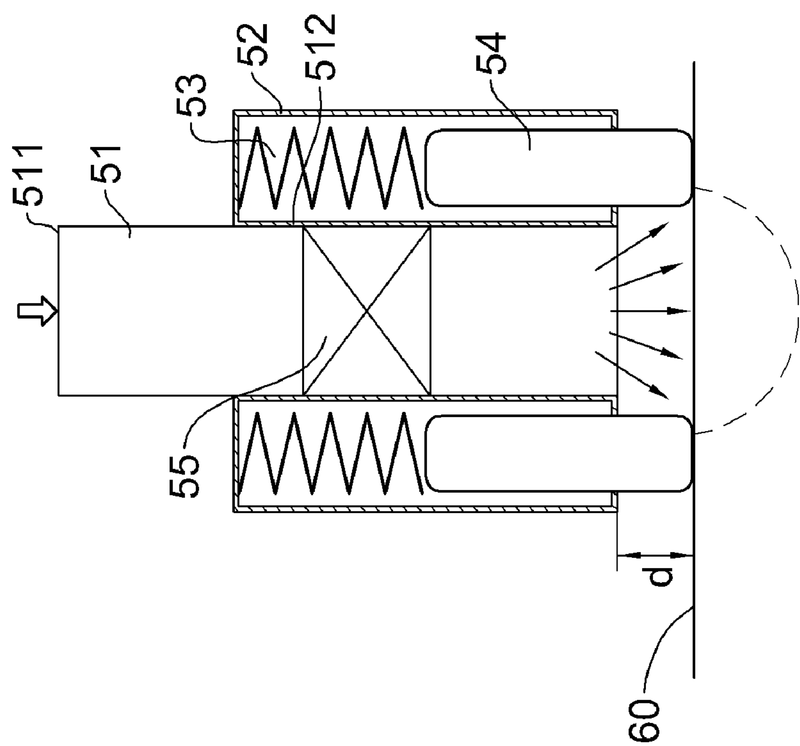
FIG. 3 is an operational side view of the acupressure jet far-infrared hydrotherapy device in FIG. 1.

With further reference to FIG. 3, the acupressure jet (50) is connected to the tip of the hose (44) and has a connector (51), a sleeve (52), at least one elastic member (53), at least one retractable post (54) and a nozzle (55). The connector (51) has an inlet (511) and an outlet (512). The inlet (511) is connected to the tip of the hose (44). The outlet (512) is for the liquid to flow out. The sleeve (52) is mounted around the connector (51) and has a top, a bottom, at least one chamber and at least one opening. The opening is formed through the bottom of the sleeve (52), is located toward the same direction with the outlet (512) of the connector (51) and communicates with a corresponding chamber. The elastic member (53) is mounted in a corresponding chamber and has an upper end and a lower end. The upper end abuts an interior surface of the top of the sleeve (52). The retractable post (54) is retractably mounted in a corresponding chamber and has an inner end and an outer end. The inner end abuts the lower end of the corresponding elastic member (53). The outer end is mounted through the corresponding opening and protrudes out the opening of the sleeve (52). The nozzle (55) is mounted at the outlet (512) of the connector (51) within the sleeve (52) to allow the flow to turn into micro drops or form an aerosol and generating a flow with an appropriate pressure P3, whereby pressure P1>P2>P3>atmosphere. According to the present invention, the retractable post (54) comprises material capable of absorbing radiation emitted by human body or photo or heat energy in nature and then emitting an far-infrared ray at a wavelength of 9 to 10 micrometer. Since that wavelength of the far-infrared ray is similar to the wavelength of radiation by human body, the far-infrared ray is easily absorbed by the human body, resulting in water resonance in human body and elevation of body temperature, thus blood circulation and metabolism of the human body is improved.

Figure 4:
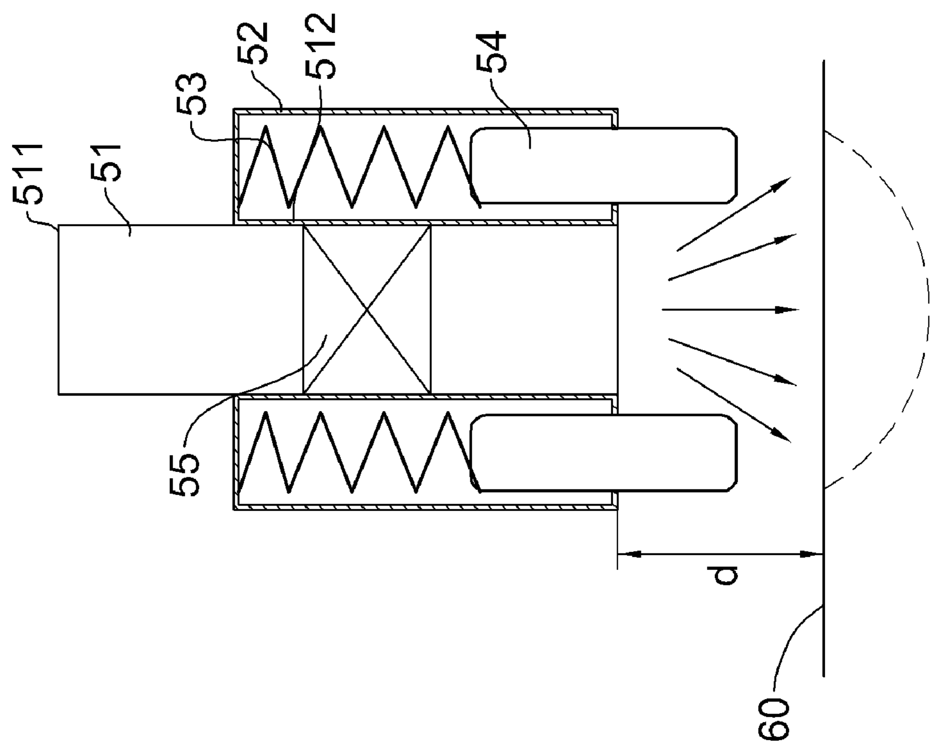
FIG. 4 is another operational side view of the acupressure jet in FIG. 3.

The acupressure jet (50) can be used under surface of the liquid in the tub (10). The flow generated by the acupressure jet (50) and applied to an acupuncture point on human body (60) forms a back pressure on the human body against the flow as means for stimulation and massage. With reference to FIGS. 3 and 4, when the outer end of the retractable post (54) presses against the human body (60), the whole acupressure jet (50) can be further pushed toward the human body (60) to a position at a distance (d) to the human body (60). The shorter the distance (d) is the higher the back pressure is and vice versa. Further, the flow generated by the acupressure jet (50) has a larger cross section than a needle, so is convenient for recognizing acupuncture points and can be moved arbitrarily.

According to the invention, the temperature controller of the heat pump (11) can be set to ensure liquid within the tub (10) is maintained at a temperature between 10 and 20° C. as a low temperature therapy with a 9~10 micrometer far-infrared ray, whereby dissolution of oxygen in the liquid is between 30 and 40 ppm.

According to the invention, the temperature controller of the heat pump (11) can be set to maintain liquid within the tub (10) at a temperature between 20 and 30° C. as a low temperature therapy with a 9~10 micrometer far-infrared ray, whereby dissolution of oxygen in the liquid is between 20 and 30 ppm.

According to the invention, the temperature controller of the heat pump (11) can be set to maintain liquid within the tub (10) to be at a temperature between 30 and 40° C. as a low temperature therapy with a 9~10 micrometer far-infrared ray, whereby dissolution of oxygen in the liquid is between 10 and 20 ppm.

As known in the art, any substances can emit far-infrared ray of various intensity. The human body with a temperature between 35 and 37° C. can generate a 9 to 10 micrometer far-infrared ray. Therefore, the far-infrared hydrotherapy device in accordance with the present invention is effective in recovering physical strength and expelling waste from human body when hydrotherapy is performed under a condition as mentioned above. In addition, liquid is recycled in the far-infrared hydrotherapy device in accordance with the present invention, thus the far-infrared hydrotherapy device in accordance with the present invention is useful for resource and cost-saving and environmental protection.

Even though numerous characteristics and advantages of the present invention have been set forth in the foregoing description, together with details of the structure and features of the invention, the disclosure is illustrative only. Changes may be made in the details, especially in matters of shape, size, and arrangement of parts within the principles of the invention to the full extent indicated by the broad general meaning of the terms in which the appended claims are expressed.

What is claimed is:

1. A far-infrared hydrotherapy device, comprising a bath unit having
- a tub having a container;
- an outlet pipe connected to the tub and communicating with the container; and
- a heat pump connected to the tub and having a temperature controller;

an oxygen supplier connected to the outlet pipe;

a booster pump connected to the outlet pipe and having an outlet;

a pressure modulator connected to the outlet of the booster pump and having
- a pressure-equalizing device, a water pressure modulating valve, a pressure-stabilizer and a hose sequentially connected; and an acupressure jet connected to the hose and having
- an inlet connected to a tip of the hose; and
- an outlet.

2. The far-infrared hydrotherapy device of claim 1, wherein the acupressure jet comprises a connector having the inlet and the outlet;

a sleeve mounted around the connector and having
- a top;
- a bottom;
- at least one chamber formed in the sleeve; and
- at least one opening formed through the bottom of the sleeve, located toward a same direction with the outlet of the connector and communicating with a corresponding chamber;

at least one elastic member mounted in a corresponding chamber and having
- an upper end abutting an interior surface of the top of the sleeve; and
- a lower end; and at least one retractable post retractably mounted in a corresponding chamber and having
- an inner end abutting the lower end of a corresponding elastic member; and
- an outer end mounted movably through the corresponding opening and selectively protruding out the bottom of the sleeve.

3. The far-infrared hydrotherapy device of claim 1, wherein the acupressure jet further comprises a nozzle mounted at the outlet of the connector.

4. The far-infrared hydrotherapy device of claim 2, wherein the acupressure jet further comprises a nozzle mounted at the outlet of the connector.

5. The far-infrared hydrotherapy device of claim 1, wherein the temperature controller of the heat pump is set to maintain liquid within the tub at a temperature between 10 and 20° C., whereby dissolution of oxygen in the liquid is between 30 and 40 ppm.

6. The far-infrared hydrotherapy device of claim 1, wherein the temperature controller of the heat pump is set to maintain liquid within the tub at a temperature between 20 and 30° C., whereby dissolution of oxygen in the liquid is between 20 and 30 ppm.

7. The far-infrared hydrotherapy device of claim 1, wherein the temperature controller of the heat pump is set to maintain liquid within the tub at a temperature between 30 and 40° C., whereby dissolution of oxygen in the liquid is between 10 and 20 ppm.

8. The far-infrared hydrotherapy device of claim 2, wherein the temperature controller of the heat pump is set to maintain liquid within the tub at a temperature between 10 and 20° C., whereby dissolution of oxygen in the liquid is between 30 and 40 ppm.

9. The far-infrared hydrotherapy device of claim 2, wherein the temperature controller of the heat pump is set to maintain liquid within the tub at a temperature between 20 and 30° C., whereby dissolution of oxygen in the liquid is between 20 and 30 ppm.

10. The far-infrared hydrotherapy device of claim 2, wherein the temperature controller of the heat pump is set to maintain liquid within the tub at a temperature between 30 and 40° C., whereby dissolution of oxygen in the liquid is between 10 and 20 ppm.

11. The far-infrared hydrotherapy device of claim 3, wherein the temperature controller of the heat pump is set to maintain liquid within the tub at a temperature between 10 and 20° C., whereby dissolution of oxygen in the liquid is between 30 and 40 ppm.

12. The far-infrared hydrotherapy device of claim 3, wherein the temperature controller of the heat pump is set to maintain liquid within the tub at a temperature between 20 and 30° C., whereby dissolution of oxygen in the liquid is between 20 and 30 ppm.

13. The far-infrared hydrotherapy device of claim 3, wherein the temperature controller of the heat pump is set to maintain liquid within the tub at a temperature between 30 and 40° C., whereby dissolution of oxygen in the liquid is between 10 and 20 ppm.

14. The far-infrared hydrotherapy device of claim 4, wherein the temperature controller of the heat pump is set to maintain liquid within the tub at a temperature between 10 and 20° C., whereby dissolution of oxygen in the liquid is between 30 and 40 ppm.

15. The far-infrared hydrotherapy device of claim 4, wherein the temperature controller of the heat pump is set to maintain liquid within the tub at a temperature between 20 and 30° C., whereby dissolution of oxygen in the liquid is between 20 and 30 ppm.

16. The far-infrared hydrotherapy device of claim 4, wherein the temperature controller of the heat pump is set to maintain liquid within the tub at a temperature between 30 and 40° C., whereby dissolution of oxygen in the liquid is between 10 and 20 ppm.

* * * * *